US00PP18786P2

(12) United States Plant Patent
White

(10) Patent No.: US PP18,786 P2
(45) Date of Patent: May 6, 2008

(54) MINIATURE ROSE PLANT NAMED 'SAVARAS'

(50) Latin Name: *Rosa hybrida minima*
Varietal Denomination: SAVaras

(75) Inventor: Wendy White, Ipswich, MA (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 0 days.

(21) Appl. No.: 11/647,012

(22) Filed: Dec. 28, 2006

(51) Int. Cl.
*A01H 5/00* (2006.01)

(52) U.S. Cl. ..... Plt./116
(58) Field of Classification Search ..... Plt./116, Plt./122
See application file for complete search history.

*Primary Examiner*—Kent Bell

(57) ABSTRACT

'SAVaras' is a new and distinct variety of miniature rose plant noted for its extremely vigorous and floriferous habit. Flowers may be a medium or medium to deep purple-red with a white reverse. The flowers last well on the plant and a mature plant can be constantly in bloom during the growing season. 'SAVaras' has a mild raspberry fragrance.

1 Drawing Sheet

CROSS REFERENCE

The rose variety of this same breeding program that most closely resembles this new invention is 'SAVachild', U.S. Plant Pat. No. 8,175. 'SAVachild' and this new invention are related and can trace many of their like qualities to a rose identified as 'Little Darling', U.S. Plant Pat. No. 1,581. In 'SAVachild', 'Little Darling' is found in the 2$^{nd}$, 3$^{rd}$, and 4$^{th}$ generations back. In this new invention, 'Little Darling' is found twice in the 3$^{rd}$ generation back and twice in the 4$^{th}$ generation back. The qualities from 'Little Darling' are vigor, profuse blooming, flowers having exhibition form, moderate fragrance, above average disease resistance.

The resemblances of this new invention to 'SAVachild', visually, both have a shade of red in the coloring of their petals; the blooms of both varieties are near the same size, when measured open at exhibition stage, around 1¾-inches; both plants are upright growing, uniformly branched, profuse blooming miniature roses.

The differences, visually, are that this new invention has a near solid pink/purple-red upper surface and a white reverse, and 'SAVachild' has primarily white petals edged with deep pink. Other distinguishing differences between 'SAVachild' and this new invention may be seen in the plant habits and petal counts: This new invention is compact and grows 15 to 20 inches tall while 'SAVachild' has a somewhat more open plant habit, growing 18 to 24 inches tall. This new invention may have anywhere from 23 to 50 petals, depending on the season or cycle of bloom (first bloom cycle usually yields the most petals while conditions such as heat and dryness tend to yield fewer petals) while 'SAVachild' uniformly has 18 to 22 petals.

Genus: *Rosa hybrida 'minima'*.

Varietal denomination: 'SAVaras'.

BACKGROUND OF THE INVENTION

The present invention relates to a new and distinct variety of hardy, bush type plant of the miniature rose class, that was created by me by crossing, as seed parent, the rose known as 'BENmfig' (not patented), and, as pollen parent, an unnamed, unpatented and unintroduced seedling from this same breeding program: 'ROzorina' (U.S. Plant Pat. No. 2,321) by 'Baby Katie' (U.S. Plant Pat. No. 4,471). The varietal denomination of this new rose is 'SAVaras'.

Idyllic goals of this breeding program were to produce unique miniature roses with the qualities of vigor, disease resistance and fragrance, along with hardiness and having exhibition, hybrid tea form blooms in abundance from spring through late fall. Roses chosen as parents for this program need to have two or more of these qualities, preferably with each quality represented at least once between the two parents.

The seed parent is a vigorous and profuse blooming pink blend, miniature rose with good disease resistance, good hybrid tea form, moderate fragrance and is a profuse bloomer. The pollen parent was a vigorous and profuse blooming orange-red miniature with very good exhibition, hybrid tea form and moderate fragrance. This cross was successful, producing this new invention, 'SAVaras', which is a vigorous and profuse bloomer with flowers having exhibition form, moderate fragrance and above average disease resistance.

The resemblance of 'SAVaras' to its parents:

All are noted as having flowers of very good exhibition form.

All are noted for flowers borne in abundance, continually throughout the growing season.

All have very good vigor.

At various times of the season, the purple-red coloring of the flowers of 'SAVaras' are similar to colors found on the flowers of its seed parent, 'BENmfig', especially in fertile soil and cooler weather when both are apt to display various tones of Magenta Rose.

'SAVaras' and its pollen parent are both noted as compact, well branched plants.

'SAVaras' is easily distinguished from its parents:

'SAVaras' is a bi-colored rose with a medium to deep purple-red upper surface and a white reverse. The colors of the blooms of the seed parent are mostly lighter shades of purple-red and its lower petal surfaces are the same colors as its upper petal surfaces and the pollen parent has orange-red flowers of solid coloring.

'SAVaras' has many more petals than either its pollen parent or seed parent.

The seed parent, 'BENmfig', grows to 3 feet tall and wide. The pollen parent grows 14 to 18 inches tall and up to 15 inches wide. 'SAVaras' grows 15 to 20 inches tall and only 10 to 14 inches wide.

Asexual reproduction by propagation by cuttings of the new variety as performed in Essex County, Mass., and San Luis Obispo County, Calif., shows that the forgoing and other distinguishing characteristics come true to form and are established and transmitted through successive propagations.

SUMMARY OF THE INVENTION

This present invention relates to a new and distinct variety of hardy, dwarf, bush type rose of the miniature class. The characteristics distinguishing it from all other varieties of which I am aware are its unique combination of flower color and fade, length of time on the plant, flower form, fragrance, petal count, plant habit and size, and degree of vigor and disease resistance. More specifically, those distinguishing characteristics are Flowers of a medium to dark purple-red upper with a white reverse and the upper aging to a Magenta Rose Flowers lasting 11 to 22 days on the plant, dependant mostly on temperature Hybrid tea form buds that open to exhibition form flowers Mild raspberry fragrance and other fragrances to a lesser degree A petal count averaging 34 but varying from 50 to 23, depending on the season and cycle of bloom An upright, well-branched, vigorous and compact plant growing 15 to 20 inches tall and 10 to 14 inches wide Flowers borne in abundance and continuously in the growing season on mature plants A plant with above average disease resistance

BRIEF DESCRIPTION OF THE DRAWING

The accompanying color photograph, taken in November, shows specimens of the buds and flowers of 'SAVaras' in different stages of development, taken from plants as grown in plastic covered greenhouses, in pots, in a mix of peat moss and coconut bark, with a controlled liquid feed system, in San Luis Obispo County, Calif.

BOTANICAL DESCRIPTION OF THE PLANT

The following observations, measurements, values and comparisons describe plants of the miniature rose class of *Rosa hybrida minima,* 'SAVaras', in the months of October and November. Plants used for this purpose were 8 to 18 month old, growing in 3½-inch plastic pots, in a mix of peat moss and coconut bark under a controlled liquid feed system, under plastic in San Luis Obispo County, Calif. 3 and 4 year old plants used for this purpose had been grown in a mixture of peat moss and vermiculite and were transferred into the ground in Essex County, Mass., three months prior to this evaluation. When a significant difference was found between plants grown in the different locations, it has been so noted. My detailed description is presented here in outline form. Color references are made using The Royal Horticultural Society Colour Chart (R.H.S.C.C.), except where common terms of color are used.

Parentage:

*I. Seed parent.*—'BENmfig' (not patented).

*II. Pollen parent.*—An unnamed, unpatented and unintroduced seedling of 'ROzorina' (U.S. Plant Pat. No. 2,321), by 'Baby Katie', (U.S. Plant Pat. No. 4,471).

Botanical classification: *Rosa hybrida 'minima'.*

Varietal denomination: 'SAVaras'.

Commercial class: Miniature; pot rose.

Commercial name: Iced Raspberry.

Flowers

Blooming habit: Fast repeat to continuous on mature plants, from late spring to late fall.

Borne: Primarily in small clusters in the spring and primarily singly during the rest of its growing season.

Bud:

*I. Size.*—7/16-inch long and ⅞-inch diameter just before the sepals divide.

*II. Form.*—Ovate with a rounded-truncate base and an acuminate apex.

*III. Color when sepals first divide.*—A. Near 56D, a very light shade of pink, on the California greenhouse grown plants. B. Near 58A, Indian Lake, on the Massachusetts outdoor grown plants.

Sepals:

*I. Color outer surface.*—A. On the California greenhouse grown plants, 138A, a medium green, and basal area and up through center, a medium to light yellow-green, near 145B, and the very tips of the outer sepals and any foliar appendages flushed with near 183A. B. On the Massachusetts grown plants, near 144B, Scheele's Green, and the entire outer sepals including the tips appendages are flushed with near 183A.

*II. Color inner surface.*—Near 138A with a basal area near 144C, medium yellow-green.

*III. Appearance outer surface.*—Matte.

*IV. Texture outer surface.*—Peppered with glands and stipitate glands but decreasing to no glands near and at the apex.

*V. Texture inner surface.*—A light covering of down.

*VI. Characteristics.*—Extend ½-inch beyond the tip of the bud, just before they divide. A. Shape of the 3 outer sepals: ovate-lanceolate. B. Shape of the 2 inner sepals: lanceolate. C. Apices of the 3 outermost sepals: lanceolate with short foliar appendages. D. Apices of the 2 innermost sepals: acuminate with smaller, short foliar appendages. E. Margins of the 2 outermost sepals: ciliate and with glands and stipitate glands and 1 or 2 foliar appendages along each side. 1. Foliar appendages of outer sepals: usually not more than 2 foliar appendages along either margin and most often they are fusiform. 2. Occasionally one of the foliar appendages may be filiform or there may be 2 filiform foliar appendages along one margin with 1 or 2 fusiform foliar appendages along the other margin. F. Margins of the 2 innermost sepals: ciliate and with glands appearing near and at the apex. G. Margins of the one sepal in-between the outer and inner: 1. One margin is as the inner sepals and one margin is as the outer sepals. 2. The one margin like those of the outer sepals may have none or one foliar appendage and that one is always filiform.

*VII. Size of the 2 outermost sepals differ as measured on each full open bloom.*—One being 5/16-inch wide and 15/16-inch long, and the other being 1/4-inch wide and 1 1/32-inch long, and on the same flower.

*VIII. Size of the 2 innermost sepals as measured on a full open bloom.*—Near equal, 17/64-inch wide and 15/16-inch long.

*IX. Size of the one sepal in-between on a full open bloom.*—9/32-inch wide and 1 1/16-inch long.

*X. Sepals roll back.*—With the petals until blooms are half open, then ahead of the petals until they are parallel with the peduncle.

*XI. Sepals drop.*—With the peduncle, after the petals drop.

Bloom:

*I. Form.*—Flat upper profile, from start to finish and a convex lower profile that flattens as the flower opens and matures.

*II. Size at exhibition stage.*—Not symmetrical, 1 3/16 by 1 1/2-inches across by 7/8-inch deep.

*III. Size when fully expanded.*—A. On the California greenhouse grown plants, size varies between 1 5/8 by 1 7/8-inches to 2 by 2 3/16-inches across and 7/8-inch deep. B. When outdoor Massachusetts grown, 1 1/2-inches across and 9/16-inch deep.

*IV. Quantity of petals.*—A. 34 to 50 on the California greenhouse grown plants. B. 23 to 24 on the Massachusetts grown plants.

*V. Quantity of petaloids.*—A. 9 to 13 on the California grown plants. B. 11 on the Massachusetts grown plants.

*VI. Fragrance.*—Slight to moderate; noticeable raspberry with other mild fragrances.

*VII. Lasting time on plant.*—6 to 8 days from when sepal divide to start of discoloration of outer petals; 11 to 22 days from when the sepals divide, to petal drop.

*VIII. Lasting quality as cut flower.*—Not tested.

Petals:

*I. Texture.*—Outside velvety; inside satiny.

*II. Form.*—A. Outer petals — broad spatulate. B. Intermediate petals — obcordate. C. Inner petals — ovato-oblong.

*III. Apex.*—A. Outer petals — cuspidate. B. Intermediate petals — entire. C. Inner petals — acute.

*IV. Base of petals.*—Obtuse.

*V. Arrangement of petals.*—Over-lapping, not evenly spaced, some appear one on top of another.

*VI. Size of outermost petals from full open flower.*—Each of the 5 outer petals are a different size, averaging about 7/8-inch wide and 1 1/16-inches long; petals of one flower may be: A. Petal one: 25/32-inch wide by 1-inch long. B. Petal two: 29/32-inch wide by 1 1/16-inches long. C. Petal three: 15/16-inch wide by 1 3/16-inches long. D. Petal four: 63/64-inch wide by 1 1/8-inches long. E. Petal five: 7/8-inch wide by 1 5/16-inch long.

*VII. Color.*—A. When petals first unfurl the predominant color of upper petal surfaces is a medium red, between 54A to 54B and 64C to 64D, on the California greenhouse grown plants and near 60D, from the Red-Purple Group, when Massachusetts outdoor grown. The basal areas of both are white, near 155D and equaling one-half to two-thirds of the petal area. The reverse of the outer petals is near 56D, a very light shade of pink, on the California greenhouse grown plants and between 62D and 69D, a very light color from the Red-Purple Group, on the Massachusetts outdoor grown plants. Both have a basal area and a streak up into the center of the petal of white, near 155D and blending into the 56D or 62D to 69D respectively. B. As the flower ages, the predominant color of the upper surface gradually lightens to a color between 57C and 66C, from the Red-Purple Group. In cooler temperatures, such as those found in Massachusetts in October and November, instead of becoming lighter, the predominant color gradually deepens to a color between 74B to 74C and 66C, from the Red-Purple Group. The basal area decreases in size to one-fourth or less of the outer petals and to about one-third of the inner petals, remaining near 155D. The reverse of all petals is white, near 155D. C. General Tonality: medium red with a white reverse on California Greenhouse grown plants; medium purple-red and medium to deep purple-red, with a white reverse when grown outdoors in Massachusetts. D. Tonality from a distance: medium red on California, greenhouse grown plants; medium to deep purple-red when grown outdoors in Massachusetts.

Receptacle:

*I. Diameter.*—A. 9/32-inch on California greenhouse grown plants. B. 7/32-inch when outdoor Massachusetts grown.

*II. Height.*—A. 9/32 to 10/32-inch on California greenhouse grown plants. B. 7/32-inch when outdoor Massachusetts grown.

*III. Profile.*—Funnel shaped.

*IV. Color.*—A. Scheele's Green, near 143A, on California greenhouse grown plants. B. 143A to 144A when outdoor Massachusetts grown.

*V. Appearance.*—Semi-glossy.

*VI. Texture.*—Smooth; glabrous.

Peduncle:

*I. Length.*—A. 1 5/16-inches on California greenhouse grown plants. B. 15/16-inch when outdoor Massachusetts grown.

*II. Diameter.*—Uniformly 3/32-inch.

*III. Aspect.*—Straight.

*IV. Strength.*—Strong.

*V. Color.*—A. Between 146D and 138C on California greenhouse grown plants. B. Near 144A when outdoor Massachusetts grown.

*VI. Appearance.*—Semi-glossy.

*VII. Texture.*—The surface is peppered with hairs and glands and with some small, soft prickles approaching the juncture with the receptacle.

*VIII. Foliar appendages at the base.*—A. There is a single or pair of leaflets at the base of the peduncle, at its juncture with the stem. B. Each appendage is either a single leaflet, a 3 leaflet-leaf or a tri-lobed leaf. C. Stipules on these appendages are attached the entire length or nearly the entire length of the petiole.

Reproductive Organs

Stamens:

*I. Arrangement.*—Regularly arranged along upper outer edge of the receptacle.

*II. Quantity.*—A. 25 to 30 on California greenhouse grown plants. B. 37 when outdoor Massachusetts grown.

*III. Filaments.*—A. Length: 5/16-inch but most often curved over so the anther is below the stigmas. B. Color: white, near 155A.

*IV. Color of anthers.*—11D, when outdoor Massachusetts grown (not recorded on California greenhouse grown plants).

*V. Pollen.*—A. Color: near 164A, when outdoor Massachusetts grown (not recorded on California greenhouse grown plants). B. Quantity: very little. C. Virility: viral.

Pistils:

*I. Quantity.*—About 16.

*II. Styles.*—A. Aspect: straight. B. Length: 6/32 to 7/32-inch, when outdoor Massachusetts grown (not recorded on California greenhouse grown plants). C. Color: 142C and 144C, when outdoor Massachusetts grown (not recorded on California greenhouse grown plants).

*II. Color of stigmas.*—White, near 155A, when outdoor Massachusetts grown (not recorded on California greenhouse grown plants).

Hips: None observed.

Plant

Habit: Upright; uniformly and well branched; compact.

Growth: Vigorous.

*I. Size of mature plant.*—15 to 20-inches tall and 10 to 14-inches wide.

*II. Length of flowering stem.*—Variable, 2½ to 5½-inches when borne singly and ¾-inch long when originating in a cluster.

Foliage:

*I. Type.*—Pinnately compound of 5 leaflets and occasionally 7 or 3 leaflets.

*II. Quantity of leaves per stem.*—Most common on flowering stem is 5 leaves, irrespective of the stem length.

*III. Length of internodes.*—Variable, 11/16 to 1 5/16-inches.

*IV. Size of mature leaf on 3-year old plants.*—3 to 3½-inches from stem to tip when measured along the rachis, 3½-inches is the most common length.

*V. Leaflets.*—A. Shape: ovate with an acute apex; the base may be either ovate or rounded. B. Size of mature terminal leaflet: up to 1⅜-inches long and 13/16-inch wide at its widest point.

*VI. Color of new foliage.*—A. Adaxial surface: 1. On the California greenhouse grown plants dark green, between 147A and 139A, and the margins and veins being flushed near 187A, from the Greyed-Purple Group and the very tips of the serrates are near 185B, a little lighter color also from the Greyed-Purple Group. 2. On outdoor Massachusetts grown plants, darker green, near 137B with the margins near 187A and the tips of the serrates near 183A. B. Abaxial surface: 1. On California greenhouse grown plants between 191A, a medium green from the Greyed-Green Group, and 144B, Scheele's Green, flushed with near 185B. 2. On outdoor Massachusetts grown plants medium green, near 138B, and flushed lightly with near 185B and heavily flushed in November.

*VII. Color of older foliage.*—(Observations are from the California greenhouse grown plants; there are currently no mature leaves to observe on the outdoor Massachusetts grown plants.) Generally the anthocyanin coloring is absent from the mature leaflets. A. Adaxial surface: very dark green, near 139A. B. Abaxial surface: near 191A and the primary and secondary lateral veins are near 139A.

*VIII. Appearance of leaflet surfaces.*—A. Adaxial surface: semi-glossy; the main vein is recessed completely and the primary lateral veins are recessed somewhat. B. Abaxial surface: matte; the main vein protrudes entirely, the primary lateral veins protrude about half-way, and the secondary laterals protrude only slightly.

*IX. Texture of the leaflet surfaces.*—A. Adaxial surface: glabrous. B. Abaxial surface: leathery.

*X. Leaflet margins.*—Serration is double.

Petiole:

*I. Size.*—13/16-inch to 1-inch long; 3/32-inch diameter.

*II. Color on young leaf.*—A. Adaxial surface: 1. On California greenhouse grown plants flushed to appear 183A, a medium shade from the Greyed-Purple Group, along the ridges and in the groove. 2. When grown outdoors in Massachusetts, very dark from the Greyed-Purple Group, near 187A along the ridge and 187B in the groove. B. Abaxial surface: 1. On California Greenhouse grown plants, near 146C, a medium yellow-green, at the base and becoming flushed with near 183B, progressing toward the rachis. 2. When grown outdoors in Massachusetts, flushed to near 187B.

*III. Color on old leaf.*—A. Adaxial surface: ridges are near 137A; the recessed area starts at the base as a light green, between 142A and 144D, and loses some of its green tone becoming, near 138B, approaching the rachis and as it becomes the groove of the petiole. B. Abaxial surface: the crest of the underside is medium yellow-green, near 145A, and blends into a medium green, near 137D along the sides.

Rachis:

*I. Size.*—Varying from ½-inch to ⅝-inch long.

*II. Color.*—A. On California greenhouse grown plants, the color of both surfaces of the rachis is the same as that part of the petiole to which it is joined, with the groove of the rachis being near 138B. B. When grown outdoors in Massachusetts, the color of the rachis on the young leaves was noted as different from that of the petiole, being a very dark color from the Greyed-Purple Group, near 187A, along the ridge and 187B in the groove; the reverse is flushed near 187A.

*III. Prickles.*—The abaxial surface has 0 to 2 prickles of a medium green, near 138B.

Petiolules:

*I. Size.*—A. Length to terminal leaflet varies from ⅜-inch to ⅝-inch. B. To the other leaflets the length is about 1/16-inch.

*II. Color.*—The same as that of the rachis with the exception being on mature foliage on plants grown in plastic pots outside in California there has been noted some flushing of near 183A on the ridges of the adaxial side and the on the entire abaxial surface.

*III. Prickles.*—On mature leaves, 1 prickle on the abaxial side of the petiolule to the terminal leaflet.

Stipules:

*I. Size/form.*—About ¼-inch attached; tips are angled out for an additional 1/16 to 3/16-inch at about a 45° angle, are slightly lunate and may be bowed by varying degrees toward or away from the stem to which the leaf is attached. A. Color: the adaxial surface is near 143A and blends into a darker green, near 137A where the edges are curled under and near 137B where the tips are angled out; the abaxial surface is near 145A. B. Margins: when young, the margins are straight and entire; as the leaf matures glands begin to appear; serrates form beneath each gland becoming serrates tipped with glands; when mature, 1 to 3 stipitate glands appear between each of those gland-tipped serrates.

Resistance: Slightly above average resistance to powdery mildew and blackspot, above average resistance downy mildew and rust.

Wood:

*I. Texture.*—New wood, glabrous; old wood, glabrous until lenticels form, generally within the first nine months of growth, that texture is corky.

*II. Appearance.*—New wood, semi-glossy; old wood, semi-glossy.

*III. Color.*—New wood, medium green between 137B and 146B; old wood, a medium yellow-green, near 146A to 146B; lenticels are between 165A and 177B, from the Greyed-Orange group.

*IV. Diameter.*—New flowering stems, 3/32-inch; old wood, 9/32-inch.

Prickles:

*I. Shape.*—Straight and angled slightly down with a tear-drop shaped base.

*II. Length.*—On main canes, 7/32 to 9/32-inch long; on laterals and flowering stems, 1/32 to 7/32-inch.

*III. Quantity.*—On main canes, 5 or 6 in two inches of stem length; on laterals and flowering stems, varying from none to numerous, each stem having a unique count.

*IV. Color.*—Mature are near 166D; young prickles are near 183B.

Hardiness: Tested hardy in zones 4 through 9, with winter protection recommended for zones 6 and colder. Plants have held up well in heat zones 10 through 1.

I claim:

1. A new and distinct variety of hardy rose plant of the miniature class is claimed, substantially as illustrated and described, characterized particularly as to novelty by the exceptionally good vigor of the plant and blooms, the distinctive color of its blooms, and the lasting quality of its blooms on the plant that is suitable for production from softwood cuttings in pots.

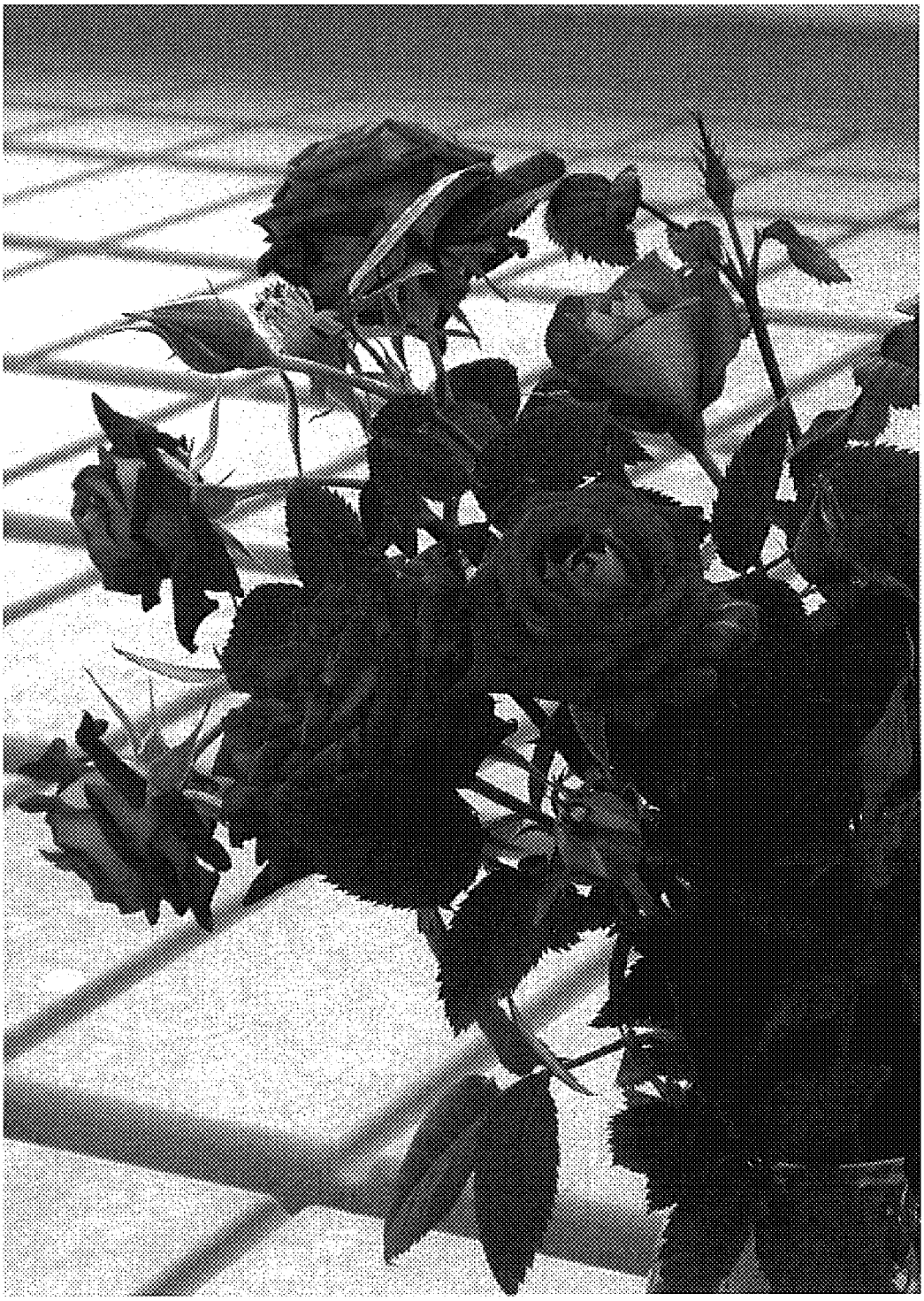

* * * * *